US008962827B2

(12) United States Patent
Jiang et al.

(10) Patent No.: US 8,962,827 B2
(45) Date of Patent: Feb. 24, 2015

(54) LINEZOLID INTERMEDIATE AND METHOD FOR SYNTHESIZING LINEZOLID

(75) Inventors: Xiaoyue Jiang, Chengguan Town (CN); Guofeng Wu, Chengguan Town (CN); Weidong Ye, Chengguan Town (CN); Runpu Shen, Chengguan Town (CN); Xiaohua Song, Chengguan Town (CN)

(73) Assignee: Zhejiang Medicine Co. Ltd. Xinchang Pharmaceutical Factory, Chengguan Town, Xinchang (CN)

( * ) Notice: Subject to any disclaimer, the term of this patent is extended or adjusted under 35 U.S.C. 154(b) by 0 days.

(21) Appl. No.: 14/008,124

(22) PCT Filed: Apr. 12, 2012

(86) PCT No.: PCT/CN2012/073897
§ 371 (c)(1),
(2), (4) Date: Sep. 27, 2013

(87) PCT Pub. No.: WO2012/139505
PCT Pub. Date: Oct. 18, 2012

(65) Prior Publication Data
US 2014/0024827 A1  Jan. 23, 2014

(51) Int. Cl.
*C07D 413/10* (2006.01)
*C07C 233/18* (2006.01)
*C07D 263/20* (2006.01)
*C07C 231/12* (2006.01)
*C07D 263/24* (2006.01)

(52) U.S. Cl.
CPC ............ *C07C 233/18* (2013.01); *C07D 263/20* (2013.01); *C07D 413/10* (2013.01); *C07C 231/12* (2013.01); *C07D 263/24* (2013.01)
USPC ........................................................ 544/137

(58) Field of Classification Search
USPC ....................................................... 544/137
See application file for complete search history.

(56) References Cited

FOREIGN PATENT DOCUMENTS

| CN | 1275122 A | 11/2000 |
|---|---|---|
| CN | 101220001 A | 7/2008 |
| CN | 101353313 A | 1/2009 |
| WO | WO-9924393 A1 | 5/1999 |
| WO | WO-02085849 A2 | 10/2002 |
| WO | WO-2010084514 A2 | 7/2010 |

OTHER PUBLICATIONS

Wei, C., et. al. "Graphical synthetic routes of linezolid," Chinese Journal of Pharmaceuticals, 41(1), 62-63 (references in article are listed on p. 69) (2010). Chinese and English translation are provided.

Brickner Sj, et al. (1996) Synthesis and Antibacterial Activity of U-100592 and U-100766, Two Oxazolidinone Antibacterial Agents for the Potential Treatment of Multifrug-Resistant Gram-Positive Bacterial Infections. J. Med. Chem., 39(3): 673-679.

Madhusudhan G, et al. (2005) A novel and short convergent approach for N-aryl-5-aminomethyl-2-oxazolidinone derivatives Linezolid and DUP-721. Indian Journal of Chemistry, 44B: 1236-1238.

Moran R, et al. (2008) Regioselective and Sterospecific Synthesis of Enantiopure 1,3-Oxazolidin-2-ones by Intramolecular Ring Opening of 2-(Box-aminomethyl)aziridines. Preparation of the Antibiotic Linezolid. Org. Lett., 10(10): 1935-38.

Xu G, et al. (2008) A Convenient Synthesis of Oxazolidinone Derivatives Linezolid and Eperezolid from (S)-Glyceraldehyde Acetonide. Heteroatom Chemistry, 19(3): 316-319.

Zhao X, et al. (2007) Improved synthesis of Linezolid. West China Journal of Pharmaceutical Sciences, 22(2): 179-181.

International Preliminary Report on Patentability issued by the International Bureau on on Oct. 15, 2013 for International Patent Application No. PCT/CN2012/073897 filed Apr. 12, 2012 and published as WO 2012/139505 on Oct. 18, 2012 (Applicant—Zhejiang Medicine Co. Ltd. Xinchang Pharmaceutical Factory; Inventors—Jiang, et al.) (5 pages).

International Search Report mailed by the International Bureau on Jul. 12, 2012 for International Patent Application No. PCT/CN2012/073897 filed Apr. 12, 2012 and published as WO 2012/139505 on Oct. 18, 2012 (Applicant—Zhejiang Medicine Co. Ltd. Xinchang Pharmaceutical Factory; Inventors—Jiang, et al.) (5 pages).

Written Opinion mailed by the International Bureau on Jul. 12, 2012 for International Patent Application No. PCT/CN2012/073897 filed Apr. 12, 2012 and published as WO 2012/139505 on Oct. 18, 2012 (Applicant—Zhejiang Medicine Co. Ltd. Xinchang Pharmaceutical Factory; Inventors—Jiang, et al.) (4 pages).

*Primary Examiner* — Rebecca Anderson
(74) *Attorney, Agent, or Firm* — Ballard Spahr LLP

(57) ABSTRACT

Provided are a linezolid intermediate and the preparation method thereof and a method for synthesizing linezolid. The structure of the intermediate is shown as formula F2, wherein the compound is prepared by a condensation reaction of (S)—N-(3-chloro-2-hydroxy-1-propyl) acetamide and the compound shown in formula F4. In the preparation methods of the compound shown in formula F2 and linezolid, the reaction system is mild, side reactions are few and the product yield is high.

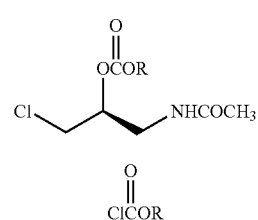

19 Claims, No Drawings

LINEZOLID INTERMEDIATE AND METHOD FOR SYNTHESIZING LINEZOLID

The present application is a National Phase Application of International Application No. PCT/CN2012/073897, filed Apr. 12, 2012, which claims the priority of China Patent Application No. 201110091844.8, filed with the Patent Office of China on Apr. 12, 2011, titled "LINEZOLID INTERMEDIATE AND METHOD FOR SYNTFIESIZING LINEZOLID", the contents of which are incorporated herein by reference in its entirety.

FIELD OF THE INVENTION

The present invention relates to the field of chemistry, particularly to an intermediate of the antibacterial drug linezolid and the preparation method thereof and a method for synthesizing linezolid.

BACKGROUND OF THE INVENTION

The chemical name of linezolid is (S)—N-((3-(3-fluoro-4-(-4-morpholinyl)phenyl)-2-oxo-5-oxazolidinyl)methyl)acetamide, and the structural formula is shown in the following figure:

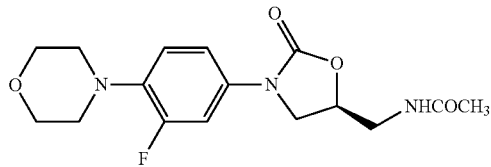

Linezolid is a fluorine-containing oxazolidine antibacterial drug developed by Pharmacia & Upjohn CoMP1100611 any, and is marketed in the United States in 2000. This drug is novel in structure and unique in mechanism of action, and is used as an antibacterial drug for the treatment of infections by multi-drug resistant Gram positive bacteria and Bacillus tuberculosis, etc. This drug has attracted much attention in the field of medicine both at home and abroad, due to that it has no cross-resistance with other antibacterial drugs, and it is expected to become another major category of novel synthetic antibacterial drugs after sulfonamides and quinolones.

There are numerous synthetic methods, of which several relatively important ones are as follows:

A. prepared by acetylation of corresponding amine or ammonium salt (Moran R, et al., Org. Lett., 2008, 10(10), 1935-38):

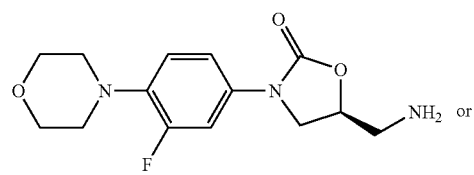

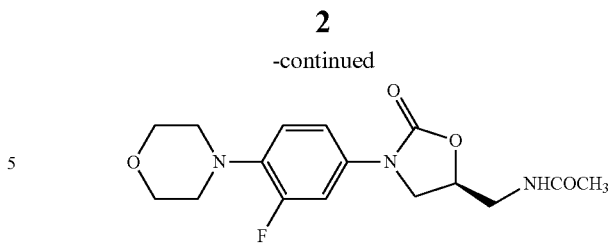

B. prepared by condensation of key intermediate N-alkoxycarbonyl-3-fluoro-4-morpholinylaniline (B1) and chiral intermediate B2 (William R, et al., WO 02085849, 2002):

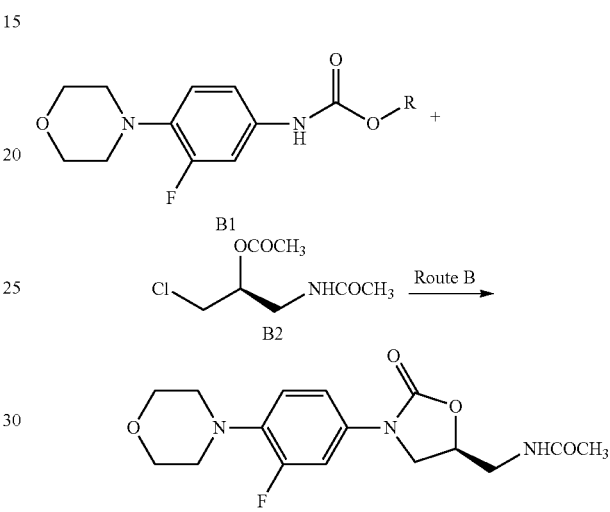

C. prepared by condensation of intermediate B1 and chiral starting material C2 to obtain the key intermediate C1, which is then transformed into the target product (refer to Brickner S. J., et al., J. Med. Chem, 1996, 39(3), 673-9):

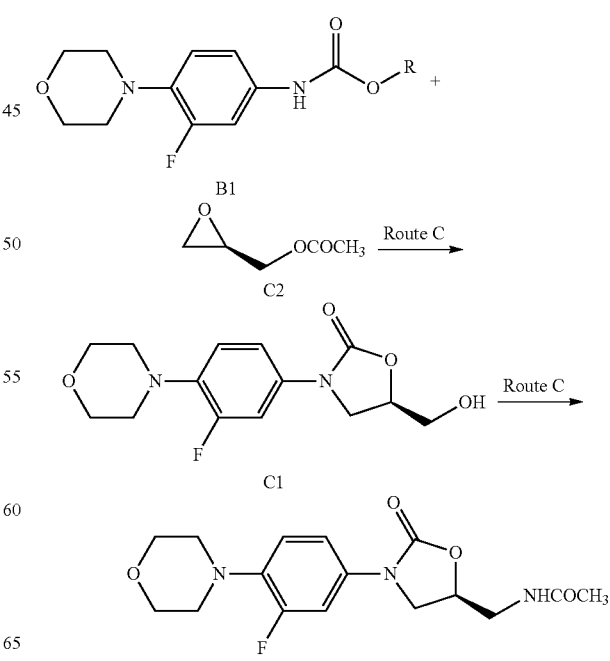

D. prepared by cyclization of key intermediate D1 and triphosgene to obtain the product (refer to China Patent CN101220001A):

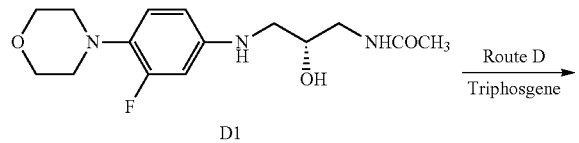

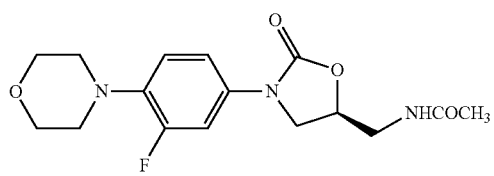

E. prepared by condensation of starting material isocyanate E2 and chiral starting material compound of formula E3 to obtain the key intermediate E1, which is then cyclized to prepare the product (B. A. Pearman: CN1275122A, 2000-11-29; B. A. Pearman: CN101353313A, 2009-01-28):

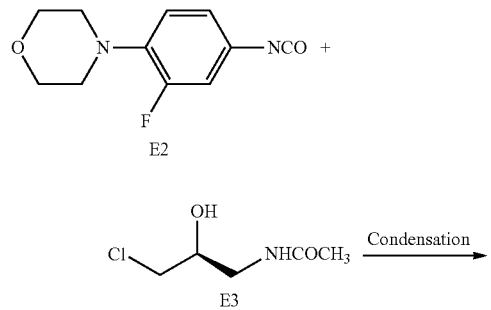

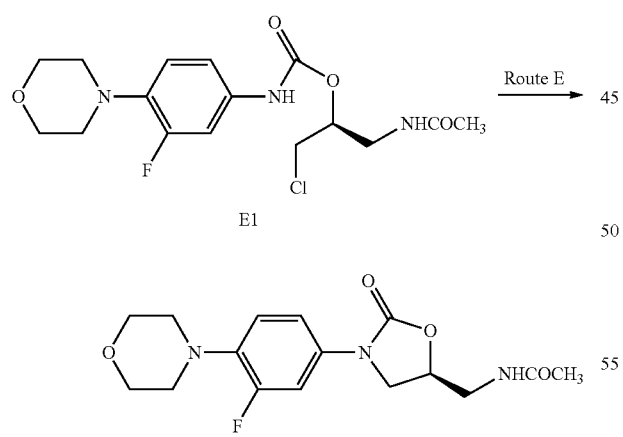

Each of the above routes has its advantages and disadvantages, and the common feature thereof is that the starting materials A1, B1, C1, D1 and E1 all contain 3-fluoro-4-morpholinylaniline group in their main structure, and as a mater of fact, 3-fluoro-4-morpholinylaniline (F1) is also the common starting material of the above-mentioned intermediates of A1, B1, C1, D1, E1, etc:

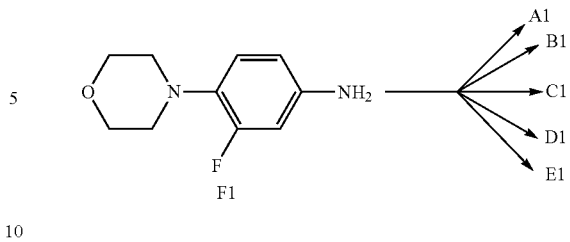

However, there is currently no report of synthesizing linezolid directly by using F1.

SUMMARY OF THE INVENTION

The purpose of the present invention is to provide a novel linezolid intermediate, and linezolid can be synthesized directly with the linezolid intermediate and 3-fluoro-4-morpholinylaniline (the compound of F1). The process route is concise, and has industrial significance.

The chemical name of the linezolid intermediate is (S)—N-(3-chloro-2-alkoxycarbonyloxy-1-propyl)acetamide, the structure thereof is of F2:

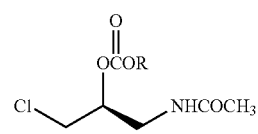

Wherein, R is hydrocarbon group.

As a preference, wherein R is alkyl or aryl.

More preferably, wherein R is methyl, ethyl, propyl or benzyl.

The present invention further provides a method for preparing the compound of F2, which is prepared by conducting a condensation reaction of (S)—N-(3-chloro-2-hydroxy-1-propyl)acetamide (the structure is represented by E3) with the compound having the structural formula of formula F4, and the reaction formula is as follows:

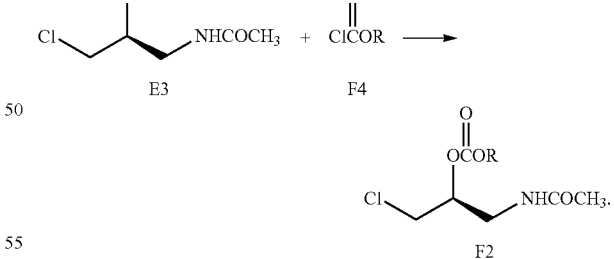

As a preference, the molar ratio of the compound of F4 to (S)—N-(3-chloro-2-hydroxy-1-propyl)acetamide is 1:1.1~1.3.

As a preference, the condensation reaction is carried out in the presence of a deacid reagent. More preferably, the deacid reagent is organic amine or inorganic base; the organic amine is triethylamine, pyridine, and the inorganic base is potassium carbonate or sodium carbonate.

As a preference, the molar ratio of the compound of F4 to the deacid reagent is 1:1.1~1.5.

As a preference, the condensation reaction is carried out in the presence of an inert solvent or a dipolar aprotic solvent. More preferably, the inert solvent is halohydrocarbon, preferably dichloromethane, chloroform, dichloroethane or chlorobenzene; the dipolar aprotic solvent is tetrahydrofuran, N,N-dimethylformamide, N,N-dimethylacetamide or acetone.

As a preference, the mass ratio of the inert solvent or dipolar aprotic solvent to (S)—N-(3-chloro-2-hydroxy-1-propyl)acetamide is 3~5:1.

As a preference, the condensation reaction is carried out at a temperature of 10° C.~40° C., preferably 15~30° C.

In the preparation of the compound of F2 according to the present invention, the condensation reaction can be traced and analyzed by using gas chromatography, liquid chromatography, thin layer chromatography and various other methods. After the reaction is completed, when using THF or acetone and other water-miscible low boiling point solvents, the solvent can be evaporated, then water and organic solvents are added to stratify, and the organic layer is dried after washing by water, then the solvents are evaporated to obtain the product; when DMF, DMA and other high boiling point solvents or dichloromethane and other water-immiscible solvents, water and organic solvents can also be added directly to stratify, then the organic layer is washed by water, dried, and recovered, to obtain the product of the compound of formula F2.

The condensation reaction is more preferably carried out at a temperature of 10° C. to 40° C., most preferably 15~30° C. When the temperature is too low, the reaction is slow, and when the temperature is too high, side reactions are apt to occur, which will reduce the yield. Water bath and other temperature control methods can be employed.

Preferably, the feeding manner of the method for preparing the compound of formula F2 according to the present invention is as follows: firstly, dissolving or suspending the starting material compound of formula E3, (S)—N-(3-chloro-2-hydroxy-1-propyl)acetamide, with 3~5 times amount of solvent, then adding a deacid reagent, and adding a mixed liquid of another starting material chloroformate and the rest solvent dropwise under heat preservation of water bath; after the completion of the dropwise adding, continuing to react for 3~4 hours, and after the completion of the reaction traced by chromatography, conducting treatment to obtain the target product of the compound of formula F2.

In the above-mentioned method for preparing the compound of formula F2, if R is methyl, ethyl or benzyl, then the starting material compounds of formula F4 are respectively methyl chloroformate, ethyl chloroformate and benzyl chloroformate, these starting materials are abundant in sources, low in costs, and have industrial significance; and when R is other substituents, the compound of formula F4 is also altered accordingly.

The present invention also provides a method for synthesizing linezolid, which is conducting a condensation reaction of 3-fluoro-4-morpholinylaniline with the compound of formula F2 in the presence of an inert solvent, to obtain linezolid:

wherein R is hydrocarbon group, preferably R is alkyl or aryl, more preferably methyl, ethyl, propyl or benzyl.

The synthetic route thereof is as follows:

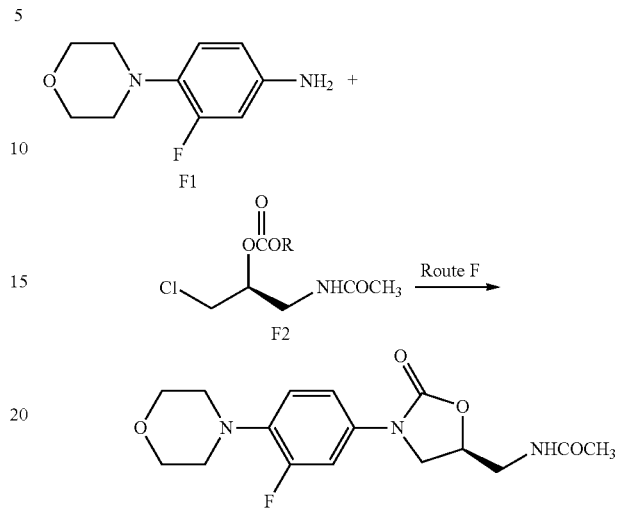

As a preference, the molar ratio of the compound of formula F2 to 3-fluoro-4-morpholinylaniline is 1.1~1.3:1.

As a reference, the reaction is carried out in the presence of an inert solvent or a dipolar aprotic solvent. More preferably, the inert solvent is halohydrocarbon, preferably dichloromethane, chloroform, dichloroethane or chlorobenzene; the dipolar aprotic solvent is tetrahydrofuran, N,N-dimethylformamide, N,N-dimethylacetamide or acetone.

As a preference, the mass ratio of the inert solvent or dipolar aprotic solvent to 3-fluoro-4-morpholinylaniline is 5~10:1.

As a preference, the reaction is carried out at a temperature of 100~160° C.

In the above-mentioned preparation method, the compound of formula F1, 3-fluoro-4-morpholinylaniline, is a common starting material, which can be prepared according to the literature method (see ZHAO Xiao-yu, et al., Improved synthesis of Linezolid, WEST CHINA JOURNAL OF PHARMACEUTICAL SCIENCES, 2007, 22(2), 179-181).

When preparing linezolid by the reaction of 3-fluoro-4-morpholinylaniline and (S)—N-(3-chloro-2-alkoxycarbonyloxy-1-propyl)acetamide compound (the compound of formula F2), the process thereof is carried out according to the following manner:

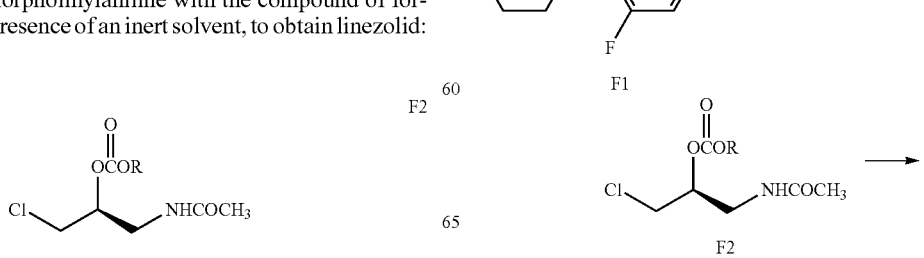

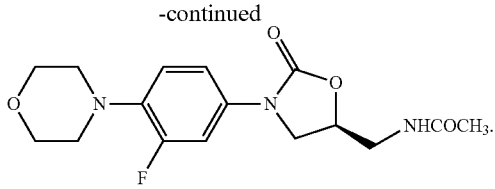

Firstly, after 3-fluoro-4-morpholinylaniline is reacted with the ortho carbon of the chlorine atom in the compound of formula F4 by nucleophilic substitution, then intramolecular cyclization reaction is carried out to obtain the product of linezolid. During such reaction, side reaction probably occurs to obtain E1:

E1

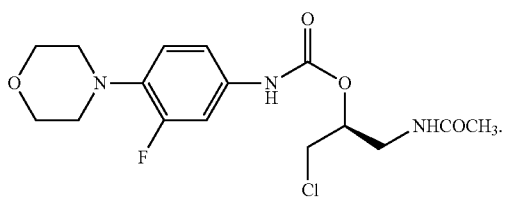

The condensation reaction of 3-fluoro-4-morpholinylaniline and the compound of formula F2 can be traced and analyzed by using liquid chromatography and thin layer chromatography and various other methods. When the reaction is completed, the solvent can be evaporated, then water and organic solvent are added to stratify, the organic layer is washed by water and dried, then the solvent is evaporated to obtain the crude product; when DMF, DMA and other high boiling point solvents are used, solid crude product can also be precipitated by adding water directly; and the crude product can be purified by column chromatography or refined by recrystallization.

The condensation reaction of 3-fluoro-4-morpholinylaniline with the compound of formula F2 is more preferably carried out at a temperature of 100° C. to 160° C. When the temperature is too low, the reaction is not easily carried out; and when the temperature is too high, side reactions are apt to occur, which will reduce the yield.

The feeding manner for the condensation reaction of 3-fluoro-4-morpholinylaniline with the compound of formula F2 is as follows: firstly, dissolving or suspending the starting material 3-fluoro-4-morpholinylaniline with preferably 4~7 times amount of solvent, then adding a mixed liquid of another starting material the compound of F2 and the rest solvent dropwise under heat preservation; continuing to react after the completion of the dropwise adding, and after the completion of the reaction traced by chromatography, conducting treatment to obtain the target product of linezolid.

Compared with the prior art, the present invention has the following advantages:
1. In the method for preparing the compound of formula F2 and the method for preparing linezolid, the starting materials for the reaction are simple, easy to prepare, and low in costs.
2. The reaction system is mild, and the side reactions are fewer.
3. The purity and yield of the product are high, and the pollutants produced by the reaction are less.

DETAILED EMBODIMENTS

The present invention discloses an intermediate of linezolid and the preparation method thereof, and a method for preparing linezolid. A person skilled in the art can learn from the contents herein, and appropriately improve the technological parameters to achieve. Specifically, all the similar substitutions and changes are obvious to a person skilled in the art, and are deemed to be included within the present invention. The method and application of the present invention have been described by preferred examples, and related personnel can obviously alter and appropriately change and combine the method and application of the present invention to achieve and apply the techniques of the present invention, without departing from the contents, spirit and scope of the present invention.

In order to further understand the technical solution of the present invention, the present invention is further illustrated below in conjunction with detailed examples.

The analytical instruments and equipments employed in the examples: NMR Spectrometer: Bruker AVANCE DMX III 400M (TMS internal standard); UV spectrometer: LabTech UV2000, silica gel plate for TLC (GF254).

EXAMPLE 1

Preparation of 3-fluoro-4-morpholinylaniline (F1)

It was prepared according to the literature method (ZHAO Xiao-yu, et al., Improved synthesis of Linezolid, WEST CHINA JOURNAL OF PHARMACEUTICAL SCIENCES, 2007, 22(2), 179-181). 36.2 g (0.16 mol) 3-fluoro-4-morpholinylnitrobenzene, 3.2 g 10% Pd/C, 30.4 g (0.49 mol) ammonium formate and 500 ml acetone were added into a 1000 ml four-necked bottle equipped with reflux condenser and dropping funnel, and stirred for 4 hours at 45~50° C. After the completion of the reaction traced by TLC (developing solvent: ethyl acetate:petroleum ether=1:1), it was cooled to room temperature. After filtering by suction, solvents were evaporated from the filtrate under reduced pressure to obtain crude solid, which was recrystallized from toluene to obtain 28.1 g solid (89.5% yield). Structural confirmation:

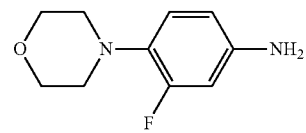 [SMILES: Nc1ccc(N2CCOCC2)c(F)c1]

$^1$HNMR (δ, ppm, 400 MHz, CDCl$_3$): 2.983 (s, 4H, (—CH$_2$—N)$_2$); 3.606 (s, 2H, NH$_2$); 3.863 (s, 4H, (—CH$_2$—O)$_2$); 6.407 (d, 1H, J=8.0, Ar—H); 6.435 (d, 1H, J=13.6, Ar—H); 6.828 (s, 1H, Ar—H);
$^{13}$CNMR (δ, ppm, 400 MHz, CDCl$_3$): 51.74, 51.76; 67.16; 103.76, 104.00; 110.60, 110.62; 120.22, 120.27; 131.64, 131.73; 142.83, 142.93; 155.53, 157.97

Example 2

Preparation of (S)—N-(3-chloro-2-hydroxy-1-propyl) acetamide Compounds (the Compound of E3)

It was prepared according to the literature method (B. A. Pearman: CN1275122A, 2000-11-29; B. A. Pearman: CN101353313A, 2009-01-28). 30 g (S)-(3-chloro-2-hydroxy-1-propyl)hydrochloride and 240 ml tetrahydrofuran were added into a 500 ml four-necked bottle equipped with thermometer and dripping funnel, and cooled to −40° C. in cold bath, and 31.5 ml triethylamine was added under stirring; after stirring for 5 min, 20.4 ml acetic anhydride was added while maintaining at −40° C., then stirred and warmed to 20~25° C. over 2 hours. After filtering, the filtrate was treated with acid magnesium silicate, then filtered under reduced pressure, and the solvent tetrahydrofuran was evaporated, and the residue was purified by flash chromatography (silica gel, gradient eluted by 75~100% ethyl acetate:cyclohexane), to obtain 26.3 g target product. Structural confirmation:

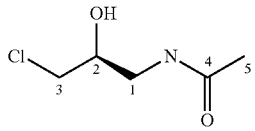

$^1$HNMR (δ, ppm, 400 MHz, D$_2$O): 1.884 (s, 3H, C$_5$H); 3.155-3.293 (m, 2H, C$_1$H); 3.443-3.582 (m, 2H, C$_3$H); 3.859-3.889 (m, 1H, C$_2$H)

$^{13}$CNMR (δ, ppm, 400 MHz, D$_2$O): 20.25; 40.19; 42.65; 69.74; 173.03

Example 3

Preparation of (S)—N-(3-chloro-2-methoxycarbonyloxy-1-propyl)acetamide Compound (F2, R is methyl)

5.1 g (0.033 mol) compound of E3, 4.55 g (0.045 mol) triethylamine and 15 ml dichloromethane were added into a 100 ml four-necked bottle equipped with thermometer and dripping funnel, and a mixed liquid of 3.82 g (0.04 mol) methyl chloroformate and 8 ml dichloromethane was added dropwise under heat preservation of water bath at 15~20° C.; and was continued to react for 3~4 hours after the completion of the dropwise adding. 20 ml water was added and stirred for 5 min, and rested to stratify. The organic layer was washed by 20 ml water and then dried by anhydrous magnesium sulfate, the dried solvent was recovered to obtain 5.4 g crude product, which is the target product F2 (R is methyl, yield 78.1%) as a colorless liquid. Structural conformation:

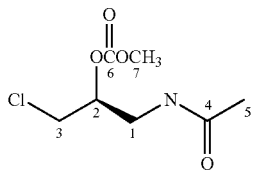

$^1$HNMR (δ, ppm, 400 MHz, D$_2$O): 2.008 (s, 3H, C$_5$H); 3.498-3.591, 3.627-3.701 (m, m, 2H, C$_1$H); 3.627-3.701, 3.724-3.766 (m, m, 2H, C$_3$H); 3.830 (s, 3H, C$_7$H); 4.943-4.995 (m, 1H, C$_2$H); 5.971 (s, 1H, —NH);

Example 4

Preparation of (S)—N-(3-chloro-2-ethoxycarbonyloxy-1-propyl)acetamide Compound (F2, R is ethyl)

5.1 g (0.033 mol) compound of E3, 5.1 g (0.065 mol) pyridine and 15 ml dichloroethane were added into a 100 ml four-necked bottle equipped with thermometer and dripping funnel, and a mixed liquid of 4.7 g (0.043 mol) ethyl chloroformate and 8 ml dichloromethane was added dropwise under heat preservation of water bath at 15~20° C.; and was continued to react for 3~4 hours after the completion of the dropwise adding. 20 ml water was added and stirred for 5 min, and rested to stratify. The organic layer was washed by 20 ml water and then dried by anhydrous magnesium sulfate, and the dried solvent was recovered to obtain 5.8 g crude product, which is the target product F2 (R is ethyl, yield 78.6%) as a colorless liquid. Structural conformation:

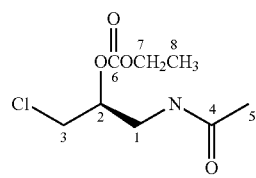

$^1$HNMR (δ, ppm, 400 MHz, D$_2$O): 1.340 (t, 3H, J=7.2, C$_8$H); 2.006 (s, 3H, C$_5$H); 3.499-3.592, 3.625-3.686 (m, m, 2H, C$_1$H); 3.625-3.686, 3.721-3.763 (m, m, 2H, C$_3$H); 4.240 (q, 2H, J=7.2, C$_7$H); 4.940-4.992 (m, 1H, C$_2$H); 5.906 (s, 1H, —NH);

Example 5

Preparation of (S)—N-(3-chloro-2-benzyloxycarbonyloxy-1-propyl)acetamide Compound (F2, R is benzyl)

5.1 g (0.033 mol) the compound of E3, 4.0 g (0.04 mol) triethylamine and 15 ml tetrahydrofuran were added into a 100 ml four-necked bottle equipped with thermometer and dripping funnel, and a mixed liquid of 6.2 g (0.036 mol) benzyl chloroformate and 8 ml tetrahydrofuran was added dropwise under heat preservation of water bath at 15~20° C.; and was continued to react for 3~4 hours after the completion of the dropwise adding. Firstly, the tetrahydrofuran was evaporated under reduced pressure, and then 30 ml dichloromethane and 20 ml water were added and stirred for 5 min, and rested to stratify. The organic layer was washed by 20 ml water and then dried by anhydrous magnesium sulfate, the dried solvent was recovered to obtain 6.9 g crude product, which is the target product F2 (R is benzyl, yield 73.2%) as a colorless liquid. Structural conformation:

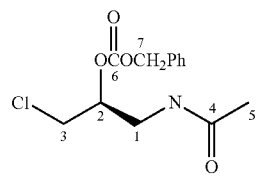

$^1$HNMR (δ, ppm, 400 MHz, D$_2$O): 2.236 (s, 3H, C$_5$H); 3.441-3.807 (m, 4H, C$_1$H, C$_3$H); 4.955-4.985 (m, 1H, C$_2$H); 5.157 (s, 2H, C$_7$H); 6.101 (s, 1H, —NH); 7.250-7.368 (m, 5H, Ar—H);

Example 6

Preparation of (S)—N-(3-chloro-2-methoxycarbonyloxy-1-propyl)acetamide Compound (F2, R is methyl) Under Different Conditions 1.52 g (0.01 mol) compound of E3, an amount of deacid reagent and 5 ml solvent (the type and quantity of the deacid reagent and solvent are shown in Table 1) were added into a 100 ml four-necked bottle equipped with thermometer and dripping funnel, and a mixed liquid of methyl chloroformate (the amount is shown in Table 1) and 2 ml the above-mentioned solvent under heat preservation of water bath at certain temperature (the temperature is shown in Table 1); and was continued to react for 3~4 hours after the completion of the dropwise adding. 10 ml water was added and stirred for 5 min, and rested to stratify. The organic layer was washed by 10 ml water and then dried by anhydrous magnesium sulfate, the dried solvent was recovered to obtain crude product, which is the target product F2 (R is methyl, and the yield is shown in Table 1) as a colorless liquid, and the NMR spectrum is the same as Example 3.

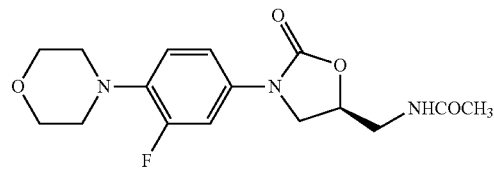

$^1$HNMR (δ, ppm, 400 MHz, CDCl$_3$): 2.024 (s, 3H, —CH$_3$); 3.055 (t, 4H, J=4.8, (—CH$_2$—N)$_2$); 3.616-3.664 (m, 2H,CH$_2$—NH); 3.773 (dd, 1H, J=9.2, J=6.8, N—(CH$_2$); 3.870 (t, 4H, J=4.8, (—CH$_2$—O)$_2$); 4.015 (t, 1H, J=8.8, N—CH$_2$); 4.62-4.778 (m, 1H, O—CH); 6.782 (t, 1H, J=4.4,

TABLE 1

Different deacid reagents and different solvents were employed to substitute triethylamine and dichloromethane, and the results are shown in the following table:

| Example | Deacid reagent Type | Molar quantity | Solvent | Methyl Chloroformate (M) | Reaction temperature (° C.) | Product (g) | Yield (%) |
|---|---|---|---|---|---|---|---|
| 6A | Pyridine | 0.011 | Chlorobenzene | 0.010 | 10 | 1.60 | 76.4 |
| 6B | Triethylamine | 0.018 | Chloroform | 0.012 | 20 | 1.72 | 82.1 |
| 6C | Potassium carbonate | 0.017 | Dimethylformamide | 0.013 | 30 | 1.53 | 73.0 |
| 6D | Pyridine | 0.013 | Tetrahydrofuran | 0.011 | 40 | 1.54 | 73.5 |
| 6E | Sodium carbonate | 0.016 | Acetone | 0.013 | 15 | 1.46 | 69.7 |
| 6F | Sodium carbonate | 0.018 | Dimethylacetamide | 0.012 | 20 | 1.48 | 70.7 |
| 6G | Sodium bicarbonate | 0.013 | Tetrahydrofuran | 0.012 | 30 | 1.45 | 69.2 |

The obtained products were combined to obtain 10.7 g crude product of F2 (R is methyl), which is used in the experiment under a condensation reaction condition in Example 10 below.

Example 7

Preparation of Linezolid by Condensation of F1 and F2 (R is Methyl)

1.96 g (0.01 mol) F1 and 15 ml DMF were added into a 250 ml four-necked bottle equipped with thermometer, reflux condenser and dripping funnel A mixed solution of 2.52 g F2 (R is methyl, 0.012 mol) and 5 ml DMF were placed into the dripping funnel, stirred, and dripped at 145~155° C. After the completion of the dropwise adding about 1 hour later, it was continued for heat preservation under stirring for 4 hours. After the completion of the reaction analyzed by TLC (developing solvent: ethyl acetate:petroleum ether=1:1), the solvent DMF was evaporated under reduced pressure, and 30 ml chloroform and 50 ml water were added into the residue, and stirred to dissolve, and rested to stratify. The organic layer was washed by water and the dried solvent was recovered to obtain 2.61 g crude product, which was recrystallized from ethyl acetate to obtain 2.46 g white solid (yield 73.0%); structural conformation:

NH); 6.935 (t, 1H, J=9.2, Ar—H); 7.085 (dd, 1H, J=8.8, J=1.6, Ar—H); 7.451 (dd, 1H, J=8.8, J=1.6, Ar—H)

$^{13}$CNMR (δ, ppm, 400 MHz, CDCl$_3$): 22.97; 41.94; 47.67; 50.98, 51.01; 66.88; 71.86; 107.34, 107.60; 113.85, 113.88; 118.85, 118.89; 133.06, 133.16; 136.27, 136.37; 154.24, 156.69; 154.31; 171.24

Example 8

Preparation of Linezolid by Condensation of F1 and F2 (R is Ethyl)

1.96 g (0.01 mol) F1 and 10 ml DMF were added into a 250 ml four-necked bottle equipped with thermometer, reflux condenser and dripping funnel A mixed solution of 2.68 g F2 (R is ethyl, 0.012 mol) and 5 ml DMF was placed into the dripping funnel, stirred, and dripped at 145~155° C. After the completion of the dropwise adding about 1 hour later, it was continued for heat preservation under stirring for 4 hours. After the completion of the reaction analyzed by TLC (developing solvent: ethyl acetate:petroleum ether=1:1), the solvent DMF was evaporated under reduced pressure, and 30 ml chloroform and 50 ml water were added into the residue, and stirred to dissolve, and rested to stratify. The organic layer was washed by water and the dried solvent was recovered to obtain 2.73 g crude product, which was recrystallized from ethyl acetate to obtain 2.52 g white solid (yield 74.5%); the NMR spectrum is the same as Example 7.

Example 9

Preparation of Linezolid by Condensation of F1 and F2 (R is Benzyl)

1.96 g (0.01 mol) F1 and 12 ml DMF were added into a 250 ml four-necked bottle equipped with thermometer, reflux condenser and dripping funnel A mixed solution of 3.43 g F2 (R is benzyl, 0.012 mol) and 5 ml DMF was placed into the dripping funnel, stirred, and dripped at 145~155° C. After the completion of the dropwise adding about 1 hour later, it was continued for heat preservation under stirring for 4 hours. After the completion of the reaction analyzed by TLC (developing solvent:ethyl acetate:petroleum ether=1:1), the solvent DMF was evaporated under reduced pressure, and 30 ml chloroform and 50 ml water were added into the residue, and stirred to dissolve, and rested to stratify. The organic layer was washed by water and the dried solvent was recovered to obtain 2.43 g crude product, which was recrystallized from ethyl acetate to obtain 2.19 g white solid (yield 67.6%); the NMR spectrum is the same as Example 7.

Example 10

Preparation of Linezolid by Condensation of F1 and F2 (R is Methyl) Under Different Conditions 0.98 g (0.005 mol) F1 and 5 ml solvent (the type and quantity of the solvent are shown in Table 2) were added into a 100 ml four-necked bottle equipped with thermometer, reflux condenser and dripping funnel, stirred, and a mixed liquid of F2 (R is methyl, the content is shown in Table 2) and certain amount of the above-mentioned solvent under certain temperature (the temperature is shown in Table 2); and was continued to react for 3~4 hours after the completion of the dropwise adding. The solvent was evaporated under reduced pressure, and 30 ml chloroform and 50 ml water were added into the residue, and stirred to dissolve, and rested to stratify. The organic layer was washed by water, and the dried solvent was recovered to obtain crude product, which is recrystallized from ethyl acetate to obtain white solid; and the NMR spectrum is the same as Example 7.

TABLE 2

Results of the condensation reaction employing different conditions

| Example | F2 amount (mole) | Solvent | Amount of solvent (ml) | Temperature of the reaction (° C.) | Amount of the product (g) | Yield (%) |
|---|---|---|---|---|---|---|
| 10A | 0.0055 | Chlorobenzene | 1 | 120 | 1.03 | 61.0 |
| 10B | 0.0060 | Chlorobenzene | 2 | 130 | 1.11 | 65.8 |
| 10C | 0.0065 | Dimethylformamide | 2 | 100 | 1.23 | 72.9 |
| 10D | 0.0055 | Dimethylformamide | 4 | 110 | 1.14 | 67.6 |
| 10E | 0.0060 | Dimethylacetamide | 3 | 160 | 1.26 | 74.7 |
| 10F | 0.0065 | Dimethylacetamide | 5 | 160 | 1.21 | 71.7 |

The above-mentioned are only preferred embodiments of the present invention. It should be noted that several improvements and modifications can also be made by an ordinary person skilled in the art without departing from the principles of the present invention, these improvements and modifications should also be deemed to be within the protection scope of the present invention.

The invention claimed is:

1. A compound of formula F2,

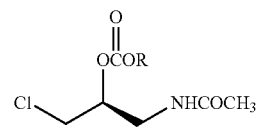

wherein R is hydrocarbon group.

2. The compound according to claim 1, wherein R is alkyl or aryl.

3. The compound according to claim 1, wherein R is methyl, ethyl, propyl or benzyl.

4. A method for preparing the compound according to claim 1, wherein the compound is prepared by a condensation reaction of (S)—N-(3-chloro-2-hydroxy-1-propyl)acetamide with the compound of formula F4:

wherein R is hydrocarbon group, preferably alkyl or aryl, more preferably methyl, ethyl, propyl or benzyl.

5. The preparation method according to claim 4, characterized in that the molar ratio of the compound of formula F4 to (S)—N-(3-chloro-2-hydroxy-1-propyl)acetamide is 1:1.1~1.3.

6. The preparation method according to claim 4, characterized in that the condensation reaction is carried out in the presence of a deacid reagent.

7. The preparation method according to claim 6, characterized in that the deacid reagent is an organic amine or an inorganic base.

8. The preparation method according to claim 7, characterized in that the organic amine is triethylamine, pyridine, and the inorganic base is potassium carbonate or sodium carbonate.

9. The preparation method according to claim 6, characterized in that the molar ratio of the compound of formula F4 to the deacid reagent is 1:1.1~1.5.

10. The preparation method according to claim 4, characterized in that the condensation reaction is carried out in the presence of an inert solvent or a dipolar aprotic solvent.

11. The preparation method according to claim 10, characterized in that the inert solvent is halohydrocarbon, preferably dichloromethane, chloroform, dichloroethane or chlorobenzene; and the dipolar aprotic solvent is tetrahydrofuran, N,N-dimethylformamide, N,N-dimethylacetamide or acetone.

12. The preparation method according to claim 10, characterized in that the mass ratio of the inert solvent or dipolar aprotic solvent to (S)—N-(3-chloro-2-hydroxy-1-propyl)acetamide is 3~5:1.

13. The preparation method according to claim 4, characterized in that the condensation reaction is carried out at a temperature of 10° C.-40° C., preferably 15~30° C.

14. A method for synthesizing linezolid, wherein the condensation reaction of 3-fluoro-4-morpholinylaniline with the compound of formula F2 is carried out in the presence of an inert solvent, to obtain linezolid:

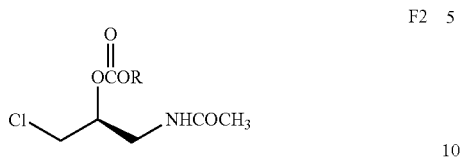

wherein R is hydrocarbon group, preferably R is alkyl or aryl, more preferably methyl, ethyl, propyl or benzyl.

15. The method according to claim 14, characterized in that the molar ratio of the compound of formula F2 to 3-fluoro-4-morpholinylaniline is 1.1~1.3:1.

16. The method according to claim 14, characterized in that the reaction is carried out in the presence of an inert solvent or a dipolar aprotic solvent.

17. The method according to claim 14, characterized in that the inert solvent is halohydrocarbon, preferably dichloromethane, chloroform, dichloroethane or chlorobenzene; and the dipolar aprotic solvent is tetrahydrofuran, N,N-dimethylformamide, N,N-dimethylacetamide or acetone.

18. The method according to claim 14, characterized in that the mass ratio of the inert solvent or dipolar aprotic solvent to 3-fluoro-4-morpholinylaniline is 5~10:1.

19. The method according to claim 14, characterized in that the reaction is carried out at a temperature of 100~160° C.

* * * * *

UNITED STATES PATENT AND TRADEMARK OFFICE
CERTIFICATE OF CORRECTION

| | | |
|---|---|---|
| PATENT NO. | : 8,962,827 B2 | Page 1 of 1 |
| APPLICATION NO. | : 14/008124 | |
| DATED | : February 24, 2015 | |
| INVENTOR(S) | : Xiaoyue Jiang et al. | |

It is certified that error appears in the above-identified patent and that said Letters Patent is hereby corrected as shown below:

On the title page, please add

Item -- (30)    Foreign Application Priority Data

April 12, 2011          (CN)..........................................201110091844.8 --

Signed and Sealed this
Twenty-second Day of September, 2015

Michelle K. Lee
*Director of the United States Patent and Trademark Office*